United States Patent
Srocka et al.

(10) Patent No.: US 10,132,612 B2
(45) Date of Patent: Nov. 20, 2018

(54) METHOD AND ASSEMBLY FOR DETERMINING THE THICKNESS OF A LAYER IN A SAMPLE STACK

(71) Applicant: HSEB Dresden GmbH, Dresden (DE)

(72) Inventors: Bernd Srocka, Berlin (DE); Stanislas Flon, Dresden (DE)

(73) Assignee: HSEB Dresden GmbH, Dresden (DE)

( * ) Notice: Subject to any disclaimer, the term of this patent is extended or adjusted under 35 U.S.C. 154(b) by 131 days.

(21) Appl. No.: 15/401,831

(22) Filed: Jan. 9, 2017

(65) Prior Publication Data

US 2017/0115112 A1 Apr. 27, 2017

Related U.S. Application Data

(63) Continuation-in-part of application No. 15/223,424, filed on Jul. 29, 2016, now Pat. No. 9,587,930.

(30) Foreign Application Priority Data

Jul. 30, 2015 (EP) .................................... 15178999

(51) Int. Cl.
    *G01B 11/06* (2006.01)

(52) U.S. Cl.
    CPC .......... *G01B 11/06* (2013.01); *G01B 2210/50* (2013.01)

(58) Field of Classification Search
    CPC ...... G01B 11/06; G01B 11/0616; G01B 11/28
    USPC ....................................................... 356/630
    See application file for complete search history.

(56) References Cited

U.S. PATENT DOCUMENTS

| 4,885,709 A * | 12/1989 | Edgar ................... B29C 47/065 250/358.1 |
| 5,072,109 A * | 12/1991 | Aguilera, Jr. .......... G02B 5/201 250/226 |
| 5,091,647 A | 2/1992 | Carduner et al. |
| 5,486,701 A | 1/1996 | Norton et al. |
| 7,151,609 B2 * | 12/2006 | Chalmers ........... G01B 11/0625 356/630 |
| 9,279,665 B2 * | 3/2016 | Kuwabara ............... H01L 22/12 |
| 2005/0006590 A1 * | 1/2005 | Harrison ................... G01J 3/02 250/372 |

(Continued)

FOREIGN PATENT DOCUMENTS

| EP | 0 545 738 A2 | 12/1992 |
| EP | 2 426 717 | 3/2012 |

(Continued)

*Primary Examiner* — Roy M Punnoose
(74) *Attorney, Agent, or Firm* — Thorp North & Western, LLP

(57) ABSTRACT

A method and assembly for determining the thickness of layers of a sample stack influencing the intensity of reflected light from a light source. The thickness is determined from the intensity detected by an array detector with a plurality of detector elements in lines and columns. The detector comprises a plurality of sections in the form of parallel stripes, the stripes detecting the light reflected by the sample stack of layers simultaneously. Light of one selected wavelength range only is detected by each of the plurality of sections of the detector. The image of the sample stack on the detector or of the parallel stripes is moved in a direction perpendicular to the longitudinal direction of the parallel stripes such that each point of the sample stack is detected at least once in each of the different wavelength ranges.

15 Claims, 12 Drawing Sheets

(56) References Cited

U.S. PATENT DOCUMENTS

| | | |
|---|---|---|
| 2013/0063733 A1 | 3/2013 | Kuwabara |
| 2014/0293295 A1 | 10/2014 | Kuwabara |
| 2015/0146193 A1* | 5/2015 | Buczkowski ...... G01N 21/6489 356/72 |
| 2016/0370174 A1 | 12/2016 | Bonino et al. |
| 2017/0038191 A1* | 2/2017 | Arieli .................. G01B 9/0209 |

FOREIGN PATENT DOCUMENTS

| | | |
|---|---|---|
| WO | WO 00 26614 A1 | 5/2000 |
| WO | WO 2014/072109 | 5/2014 |

\* cited by examiner

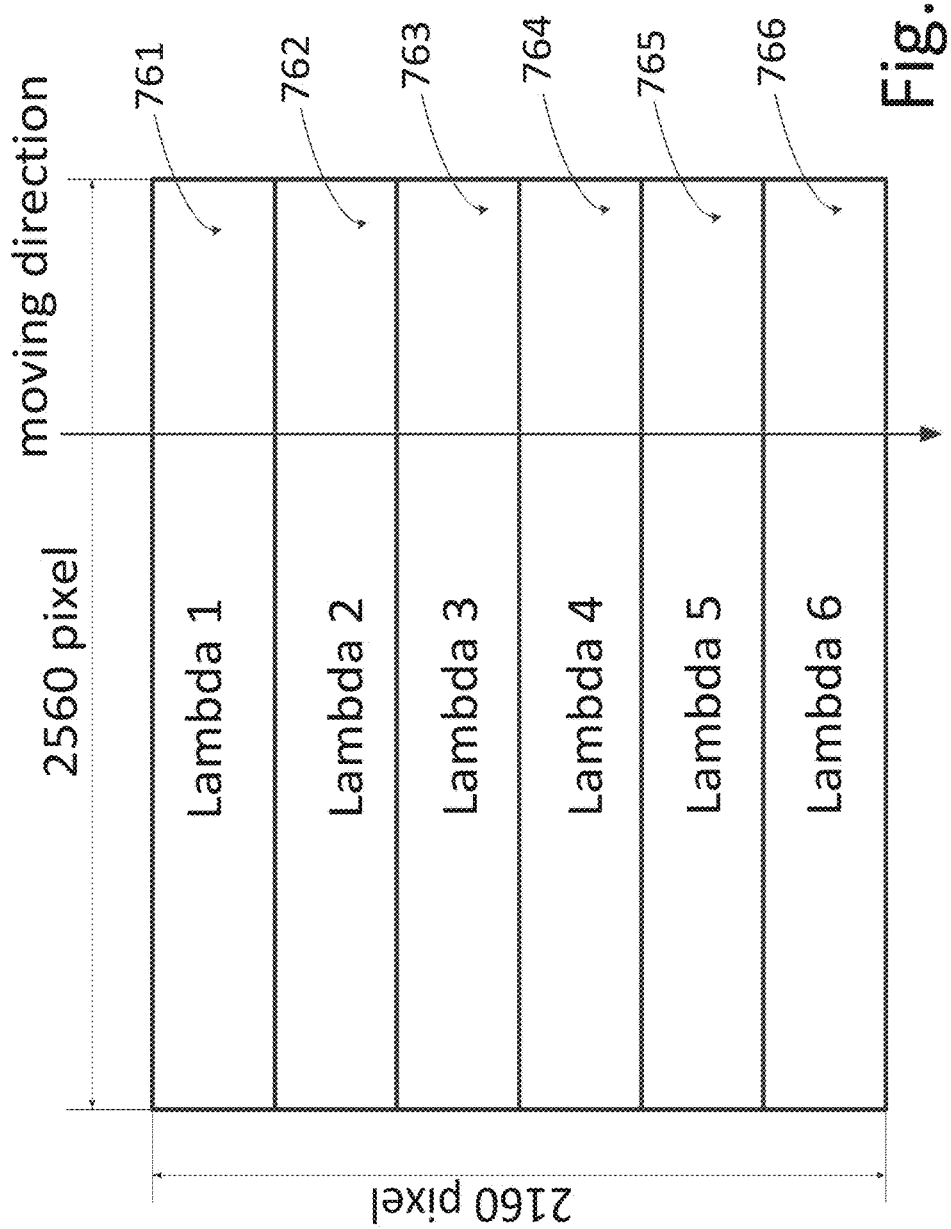

METHOD AND ASSEMBLY FOR DETERMINING THE THICKNESS OF A LAYER IN A SAMPLE STACK

RELATED APPLICATIONS

This is a continuation-in-part of co-pending application Ser. No. 15/223,424, filed Jul. 29, 2016, entitled Method and Assembly for Determining the Thickness of a Layer in a Sample Stack, incorporated herein in its entirety by reference.

TECHNICAL FIELD

The invention relates to a method for determining the thickness of one or more layers of a sample stack of layers or other properties influencing the intensity of light reflected by the sample stack with an assembly comprising a light source for illuminating the sample stack of layers and a camera with a detector for detecting the intensity of light reflected by the sample stack of layers in defined wavelength ranges, the method comprising the steps of:
(a) illuminating the sample stack of layers with light from the light source;
(b) detecting the intensity of light reflected by the sample stack of layers with the detector in different wavelength ranges; and
(c) determining the thickness or other property from the intensity detected by the detector.

Furthermore, the invention relates to an inspection assembly for determining the thickness of one or more layers of a sample stack of layers or other properties influencing the intensity of light reflected by the sample stack comprising:
(a) a light source for illuminating the sample stack of layers; and
(b) a camera with a detector for detecting the intensity of light reflected by the sample stack of layers in defined, different wavelength ranges; and
(c) computing means for determining the thickness or other property from the intensity detected by the detector.

In different branches of the industry flat products are inspected with optical methods regarding their properties. In the semiconductor- and solar cell industry these are amongst others wafers and solar cells. Wafers are discs of semiconductor, glass, sheet or ceramic materials. Such inspected properties may be the thickness of layers on the surface of the objects. Other inspected properties may be the material composition of certain layers formed by mixtures of materials. An example of such a mixture is $Si_{1-x}Ge_x$ which is used to produce strain in a semiconductor transistor. Layers of different materials are used, for instance, for the production of electronic semiconductor devices ("chips"). Those stacks may contain up to ten layers depending on the specific technology used.

A particular field of interest is the fabrication of special wafers, so called SOI wafers, used for modern semiconductor devices. Current technology wafers have a double layer on the top surface. The wafers are composed of a silicon oxide layer and a silicon layer on top of it. In a modern approach regarding new devices especially with lower power and/or high performance the two layers have a thickness in the range of several nanometers. The very small layer thicknesses strongly influence the performance of the chips produced on the wafers. Their accuracy and lateral homogeneity are, therefore, very important for the chip manufacturing process and the later device performance. It is, hence, of particular interest to measure the thickness of a layer and its homogeneity during the manufacturing process with high lateral resolution, high accuracy and within a short time per wafer.

Similar requirements must be fulfilled in other fields. The thickness and lateral homogeneity of layer stacks may be of crucial importance for end product parameters.

PRIOR ART

Ellipsometric measurements for nondestructive layer analysis are known in the art. A sample is illuminated with polarized light. The light is reflected at the interfaces between the layers or transmitted by the layers and finally detected. The properties of the layers are determined by the change of the polarization state of the detected light. Such measured values depend very much on the focus position and the inclination of the surface of the sample. The method is highly accurate and can be adapted to very complex layer stacks with many layers involved if an appropriate layer model is used. Such a method is, however, time consuming requiring several seconds per point and its spatial resolution is restricted to a few tens of um. Hence, ellipsometric measurements are limited in the field of production control.

A similar consideration applies to the method of spectral reflectometry. Spectral reflectometry can be performed either by the use of spectrometers or with so called hyperspectral imaging cameras. Spectrometers provide spectral reflectance data in several hundreds to thousands of wavelength points. Hyperspectral imaging cameras provide reflectance data in the range of about 12 to about 256 wavelength points. Both methods can be used for a quite broad range of thickness values and provide accurate results. The obtained results strongly depend on the number of wavelength data points used, but are much too slow for a high speed and high resolution mapping.

Patent publications WO2014072109, EP2426717, U.S.2014293295, and U.S.2013063733 disclose the determination of the thickness of one layer (film) of a double layer stack only using the measurement of the intensity of the reflected light. The disclosed methods are useful for a measurement where the nominal thickness of both layers is known and only small deviations from such nominal thickness values shall be determined. The key idea in all three publications is to restrict the measurement to a small wavelength range selected in such a way that the influence of the second layer is minimal. The deviation of the intensity of the reflected light versus thickness variation is nearly zero within the selected small wavelength range. This idea is based on the fact that the intensity of the light reflected by a two layer stack on top of a substrate varies strongly with the wavelength range due to the interference of the optical waves in dependence of the thicknesses of the layers.

The described methods differ in terms of how to get a good reference for the calibration of the method and which is the best way to avoid influences from the second layer. The methods can be used either for the top or the bottom layer within the inspected double layer stack selecting different appropriate small wavelength ranges. However, all methods mentioned above lack on the fact that they assume that the influence of the second layer thickness variation is neglectable within the selected wavelength range. In reality however, it may not be neglected and for a high resolution method the influence of the second layer can be as high as several percent, rendering the measured result to be useless.

Patent application EP15178999 (not published) by the applicant discloses a method to determine the thickness of both layers of a double layer system, such as a SOI wafer. This is achieved by measuring the reflectance of the layer stack in two appropriate wavelength ranges. The simultaneous measurement in different wavelength ranges is carried out by using a beamsplitter to generate two optical paths. The different wavelength ranges are then selected with two filters. It is also disclosed to use gratings or prisms to select a suitable wavelength range. The intensity of the light is distributed on the two measurement channels which compromises the signal-to-noise ratio. The known assembly requires many optical components.

The general physics of the wave reflection at interfaces between two materials are described by Fresnel formulas. According to the formulas the dependency of the travelling speed and field amplitude of electromagnetic waves inside a material and along its interfaces on the material parameters are well known in the art. The most crucial problem for a theoretical description of the wave propagation is the accurate knowledge of the material parameters. An example of such a material parameter is the refraction index. While the Fresnel formulas accurately describe the propagation across smooth, ideal material interfaces it may be even more complex to correctly consider the surface roughness effects. In practical solutions, therefore, calibration procedures are required to complement first principle physics.

The refraction index is given as a complex value describing the refraction and the absorption. The method is summarized, for instance, in WO2014072109. It is the basic idea of the prior art inspection methods to use the light reflected by a sample stack within small wavelength ranges where the influence of the second layer is minimal.

The influence of the two layers within a small thickness range can be described by approximated relations. A simple example of the prior art uses a layer stack of two layers named, for example, A and B. Each of the layers of the two layer stack has a nominal thickness. A Taylor series at the point of the nominal layer thicknesses of layer A and B can be used to calculate the reflected light intensity R:

$$R = R_0 + \frac{\partial tR}{\partial t_A}\Delta t_A + \frac{\partial tR}{\partial t_B}\Delta t_B + \frac{\partial^2 tR}{\partial t_A^2}(\Delta t_A)^2 + \frac{\partial^2 tR}{\partial t_B^2}(\Delta t_B)^2 + \frac{\partial^2 tR}{\partial t_A \partial t_B}\Delta t_A \Delta t_B + \quad (1)$$

wherein
- $t_A$: thickness of layer A
- $t_B$: thickness of layer B
- $t_{A0}$: nominal thickness of layer A
- $t_{B0}$: nominal thickness of layer B
- R: actual reflected light intensity measured at the point where layers A and B have the thickness values $t_A$ and $t_B$.
- $R_0$: reflected light intensity where each layer has the nominal thickness, i.e. $t_A=t_{A0}$ and $t_B=t_{B0}$ $$\frac{\partial x}{\partial y} \text{ and } \frac{\partial^2 x}{\partial y^2}$$

denote partial derivatives of first or second order, respectively, taken at the point where the layers A and B have their nominal thickness values
- $\Delta_A$ denotes the difference $\Delta t_A = t_A - t_{A0}$;
- $\Delta_B$ denotes the difference $\Delta t_B = t_B - t_{B0}$.

The reflected light intensity R varies over the wavelength due to the interference of the optical waves in dependence of the thicknesses of the two layers. The selection of a wavelength range where the influence of one of the layers, for example layer B, is neglectable as it is necessary in prior art measurements means that a wavelength range must be found where $$\frac{\partial R}{\partial t_B}$$

is nearly zero while $$\frac{\partial R}{\partial t_A}$$

is not zero. Expressed more exactly $$\frac{\partial R}{\partial t_B}$$

must be much smaller than $$\frac{\partial R}{\partial t_A}.$$

If higher orders of derivatives are neglected, since their influence is usually smaller in a Taylor series, the equation (1) then reads:

$$R = R_0 + \frac{\partial R}{\partial t_A}\Delta t_A + \frac{\partial^2 R}{\partial t_A^2}(\Delta t_A)^2 \quad (2)$$

Such a relation can be easily used to determine the layer thickness $t_A$ assuming that $t_B$ has its nominal value $t_B=t_{B0}$ and has, therefore, neglectable influence on R. The thickness of layer A can be determined by using a calibration method for the relation between R and $t_A$. For the calibration layer stacks are manufactured with $t_B=t_{B0}$ and $t_A$ with several thickness values around $t_{A0}$. The layer stack samples are then measured by a reference method, e.g. ellipsometry with high accuracy. A calibration curve $R=f(t_A)$ can then be created from the measured intensity values at the measured points. This method is disclosed in above mentioned WO2014072109. The method has the disadvantage that layer B is assumed to be exactly at its nominal value $t_B=t_{B0}$ at all points. The influence of the thickness of layer B is entirely neglected. This neglection causes a systematic error of the determined thickness $t_A$ of layer A, which cannot be resolved within the known methods.

The same consideration holds vici versa for a determination of layer thickness $t_B$ under the assumption that $t_A$ has its nominal value $t_A=t_{A0}$.

DISCLOSURE OF THE INVENTION

It is an object of the invention to provide an assembly and a method of the above mentioned kind which allows an accurate measurement of the thickness of one or more layers simultaneously with high accuracy, high speed and in the single micron and sub-micron lateral resolution range. It is a further object of the invention to determine the thickness of one or more layers in a sample stack in a time and cost efficient way avoiding extensive spectral evaluation methods like ellipsometry or spectral reflectometry as commonly used.

According to the invention this object is achieved with the method of the above mentioned kind, which is characterized in that:

(d) the detector is an array detector with a plurality of detector elements in lines and columns;

(e) an image of the sample stack of layers is generated on the detector;

(f) the detector comprises a plurality of sections in the form of parallel stripes, the stripes detecting the intensity of light reflected by the sample stack of layers simultaneously;

(g) light of one selected wavelength range only is detected by each of the plurality of sections of the detector; and (h) a movement of the image of the sample stack of layers on the detector or of the parallel stripes is generated in a direction perpendicular to the longitudinal direction of the parallel stripes such that each point of the inspected sample stack of layers is detected at least once in each of the different wavelength ranges.

The object is also achieved with an inspection assembly of the above mentioned kind which is characterized in that (d) the detector is an array detector with a plurality of detector elements in lines and columns;

(e) optical means are provided for generating an image of the sample stack of layers on the detector;

(f) the detector comprises a plurality of sections in the form of parallel stripes, the stripes adapted to simultaneously detect the light reflected by the sample stack of layers;

(g) filter means are provided for transmitting only light of one selected wavelength range to only one of each of the plurality of sections of the detector or detector elements adapted to measure light of one selected wavelength range only in each of the plurality of sections; and (h) moving means are provided for moving the image of the sample stack of layers on the detector or of the parallel stripes in a direction perpendicular to the longitudinal direction of the parallel stripes such that each point of the inspected sample stack of layers is detectable at least once in each of the different wavelength ranges.

The stripes on the detector may either be a series of lines or a series of columns. Such lines or columns may be, in particular, neighboring lines or columns. The achieved result does not depend on the definition of the stripes in this respect. The stripes extend from one side of the detector to the opposite side of the detector. Detectors, where each image point consists of 4 color sensitive detector elements as it is the case with RGB (red-green-blue)-detectors are not suitable for the present invention.

The light source preferably has a continuous wavelength spectrum extending over all wavelength ranges which are used for the inspection. It is not necessary that the emission spectrum has an even intensity distribution, but it is essential that light is emitted in or converted to all considered wavelength ranges. Suitable continuum sources have a spectrum, for example, extending from the near UV to VIS in the range between 400 nm and 800 nm. Such wavelength range is suitable for the thicknesses commonly used for layers in the wafer production. Obviously, if the thicknesses vary beyond what is presently used in this field, the wavelength range may differ. It is, however, also possible to use more than one light source and combine their light to achieve sufficient coverage of the considered wavelength ranges. The width of the wavelength range may be represented by the halfwidth, i.e., the wavelength range with an intensity larger than half of the maximum intensity value. Such width is selected such that the intensity of the light is sufficient to provide a good signal-to-noise ratio but still small enough to allow good accuracy. A halfwidth of, for example, 5 to 20 nm may be suitable in the above wavelength range.

An imaging optical set-up with components such as mirrors or lenses is used to generate an image of the sample stack of layers on the detector array. The optical path may have intermediate imaging planes, but they are not necessary. The image may be generated with any suitable imaging ratio to obtain a good signal-to-noise ratio and sufficient high resolution with an affordable detector.

A relative movement of the image is generated perpendicular to the longitudinal direction of the stripes between detection steps, i.e. between taking an image. The relative movement can be effected in numerous different ways. It is possible to move the carrier of the sample stack of layers. It is also possible to move the camera with the detector. Other alternatives only move the image without moving the sample stack of layers or the camera, by means of, for example, a moveable mirror in the optical path. Another alternative provides that a filter as described below is moved perpendicular to the stripes. All alternatives can also be combined. There is only a condition that there is at least a portion of the movement perpendicular to the longitudinal direction of the stripes. The movement enables that each detector element detects a different wavelength range of the same image point.

The stripes may cover the entire image at one stage. The stripes pass along the image of the object or vice versa whereby all image points are measured in all wavelength ranges. The measurements of the entire detector array are used. Only when the filter is in the range of the edges of the image of the object there will be n−1 measurements without full use of the detector array, where n is the number of used wavelength ranges.

Similar to the two-layer stack described above the influence of the layers in a layer stack with a plurality of layers within a small range of thickness variation can be described by approximated relations. A simple example uses a layer stack of n layers. Each of the layers of the n layers in the stack has a nominal thickness $t_{i0}$ where i goes from 1 to n. A Taylor series at the point of the nominal layer thicknesses of all layers can be used to calculate the reflected light intensity R:

$$R = R_0 + \sum_{i=1}^{n} \frac{\partial tR}{\partial t_i} \Delta t_i + \sum_{i=1}^{n} \frac{\partial tR}{\partial t_i} \Delta t_i * \sum_{j=1}^{n} \frac{\partial tR}{\partial t_j} \Delta t_j + \quad (1)$$

wherein:

$t_{i,j}$: thickness of layer i respectively j $t_{i0}$: nominal thickness of layer i R: actual reflected light intensity measured at the point where the layers deviate from their nominal thickness values $t_{i0}$ by $\Delta t_i$ $R_0$: reflected light intensity measured at the point where all layers have their nominal thickness values $t_{i0}$.

$$\frac{\partial x}{\partial y} \text{ and } \frac{\partial^2 x}{\partial y^2}$$

denote partial aenvatives of first or second order, respectively, taken at the point where all layers B have their nominal thickness values $\Delta t_j$, denotes the difference $\Delta t_i = t_i - t_{i0}$ The reflected light intensity R detected by the detector element varies over the wavelength due to the interference of the optical waves in dependence of the thicknesses of the layers in the stack. In order to determine n independent parameters, such as the thickness values for the n layers, a series of n independent measurements is required. Without restricting the general idea a film composition variable, such as the composition index in the $Si_{1-x}Ge_x$, can be considered in a similar manner as a film thickness. The only difference is that the partial derivatives in equation (1) is dThickness/dComposition and not against a thickness value. In that sense $t_{i,j}$ above may be also a material composition instead of a thickness value.

The knowledge of all partial derivatives in equation (1) either from theoretical calculations or from calibration measurements using reference samples with known thicknesses and compositions allows determining exactly all n unknown parameters $t_i$ based on the result of n independent measurements. With n measurements equation (1) represents a set of n independent linear equations for the n derivatives $\Delta t_j$ which can be solved by common linear equation set algorithms. Such an algorithm may be, for example, the Gauβ-Jordan method.

In the case that less, such as just one or two unknown parameters representing the thickness or the material composition shall be determined and for a well restricted parameter range the result can even be obtained with the measurement at a plurality of wavelengths without calibration, just based on the theoretical known dependency of R on the unknown parameters.

With the present invention it is possible to determine the thicknesses of n layers in a layer stack accurately. The measurement in n different wavelength ranges requires the use of n series of calibrating curves. One series for each wavelength range is needed. Each series provides information about the intensity of the reflected light under known thickness and composition conditions. If two or more thicknesses shall be determined, the combination of the thicknesses of the different layers of a stack belonging to one specific reflectivity is not unambiguous. It is an important feature of the invention that such a combination can be found by using different wavelength ranges. The term wavelength range means the range which can be represented by one single wavelength value, i.e. the range transmitted by an interference filter or the like and is not meant to extend far beyond several tens of nanometers.

The intensity of the light reflected by a stack of layers is detected simultaneously or quasi simultaneously for n wavelength ranges. Thereby, the measurements can be carried out fast and variations of the set-up will not have any influence. Also, it turns out to be useful to use normalized values by subtracting dark values and normalizing the measured intensities by a reference value which is, for example, taken from the reflection at a well known and stable reference material target.

In a preferred embodiment of the invention the detector elements in the same section of the detector are sensitive to one of the different wavelength ranges only. This means, that a first stripe is sensitive for a first wavelength range and the second stripe for a different, second wavelength range and so on.

In an alternative embodiment of the invention the light in the optical path between the light source and the detector is filtered by a plurality of different bandpass filters in a striped geometrical order, each bandpass filter transmitting light in one of the selected wavelength ranges only and positioned in the object plane, the detector plane, an intermediate image plane or any other plane conjugated to the object.

A very suitable set-up of the invention uses a high performance scientific camera with a high dynamic range, high resolution (high pixel count) and high speed. In order to accomplish the wavelength range set the detector may be combined with a filter set composed of n bandpass filters. The filter assembly divides the detector area into n stripes of different sensitivity. It provides n band pass filters to form n sections in the form of stripes with sensitivities to an individual wavelength range. After each illumination of the detector and signal acquisition the image is relatively moved. If, for example, the moving distance is 1/n-th of the overall detector length in the direction perpendicular to the stripes after n steps the reflectance intensities in all n wavelength ranges are determined by the detector for the whole field of view of the camera and stored in a computer. From this information the thickness of the up to n layers or composition parameters can be calculated using the stored reference information and/or the calibration curves as described above.

Selecting specific filters for certain layer combinations can improve the selectivity of the signal in each wavelength range to a certain layer or layer combination and improve the signal to noise ratio. This invention provides to use a fixed filter set and divide the useful sensitivity range of the detector into a series of n wavelength ranges. With such a set up a wide variety of layer stacks can be measured with sufficient accuracy. Using a fixed filter set also reduces the complexity of the set-up with increased stability. This fixed set up may be as well used for a system of less unknown parameters, e.g. a layer stack of just 2, 3 or 4 layers. In such an application the additional measurement values provide an over-sampling of the system in terms of measured quantities and may serve conveniently to improve the robustness of the measurement by using them within a best fit approach.

It is known to use wavelength filters in an optical path. Such optical filters, however, generally have only one wavelength range. In order to avoid imaging of dirt and scratches on the filter, such known filters are positioned outside of any image planes. Contrary to such known filters the present invention uses a plurality of wavelength ranges by, for example, a plurality of wavelength filters. Such filters are positioned in an image plane. Defects of the filters present in all images will be removed by means of image processing methods.

If the filter stripes are provided in an intermediate image plane, it may be useful to use a filter with two sets of stripes, i.e. two stripes for each wavelength. In such a way the edges may be measured easily without having to change the moving direction.

A preferred modification of the invention provides that a series of images are taken with the detector and a movement of the image of the sample stack of layers on the detector or a movement of the parallel stripes is generated before each of the images is taken, the length of the movement corresponding to the width of the sections on the detector. It is, however, also possible to take more than one image of the sample stack between the movements. It is preferred to always move the image or filter in the same direction in order to obtain all information as fast as possible.

According to a preferred modification of the invention the amount of different wavelength ranges is identical to the amount of stripes. Thereby, a minimum of transitions between the stripes is achieved. The stripes all may have the same width.

According to one alternative of the invention the sample stack of layers has less layers than wavelength ranges and the thickness and/or other property of at least one layer is determined from two or more measurements. Each additional measurement with another wavelength range will improve accuracy or enable better determination without calibration measurements. In such a case it is possible to determine the thickness and/or other property of at least one layer from a plurality of measurements without a measured calibration curve. A plurality of measurements for determining the thickness and/or other property of only one layer may, however, also be used to improve the accuracy by fitting the determined values.

A modification of the invention may provide that the thickness and/or other property determined without a measured calibration curve is calculated using theoretical values of material properties of the layers.

Another alternative modification of the present invention provides that a measured calibration curve is used for each inspected layer to determine the thickness and/or other property. Thereby, stacks of up to n layers may be inspected.

Further modifications of the invention are subject matter of the subclaims. An embodiment is described below in greater detail with reference to the accompanying drawings.

BRIEF DESCRIPTION OF THE DRAWINGS

FIG. 4a is a schematic view of the broadband filter means used in the assembly of FIG. 1.

DESCRIPTION OF THE EMBODIMENTS

1. Embodiment: Measurement of a Two-layer Stack at 6 Different Wavelengths

Figure 1A:
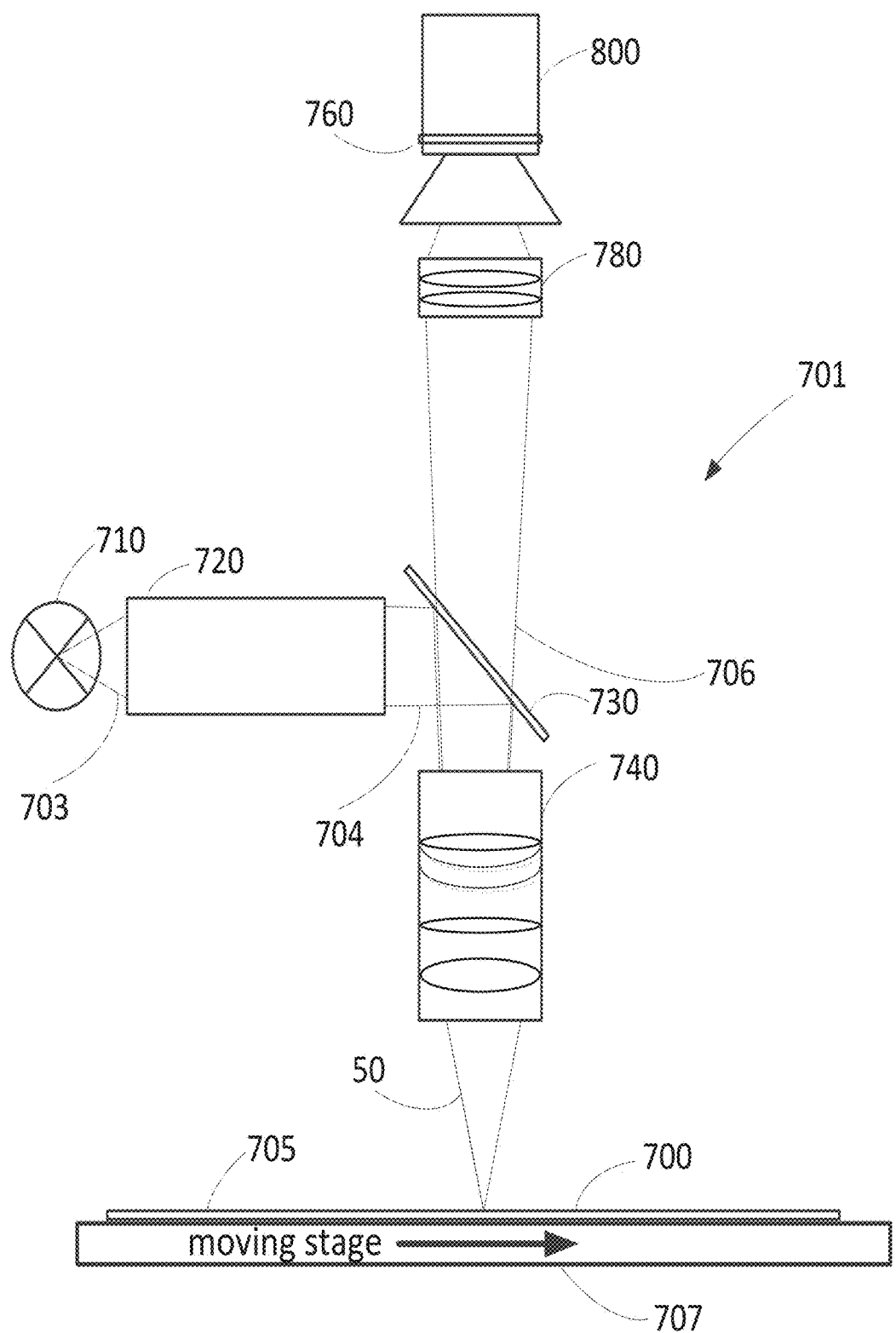
FIG. 1a is a schematic illustration of a device for measuring reflectivity at different wavelengths simultaneously with a filter set in the detector plane.
Figure 1B:
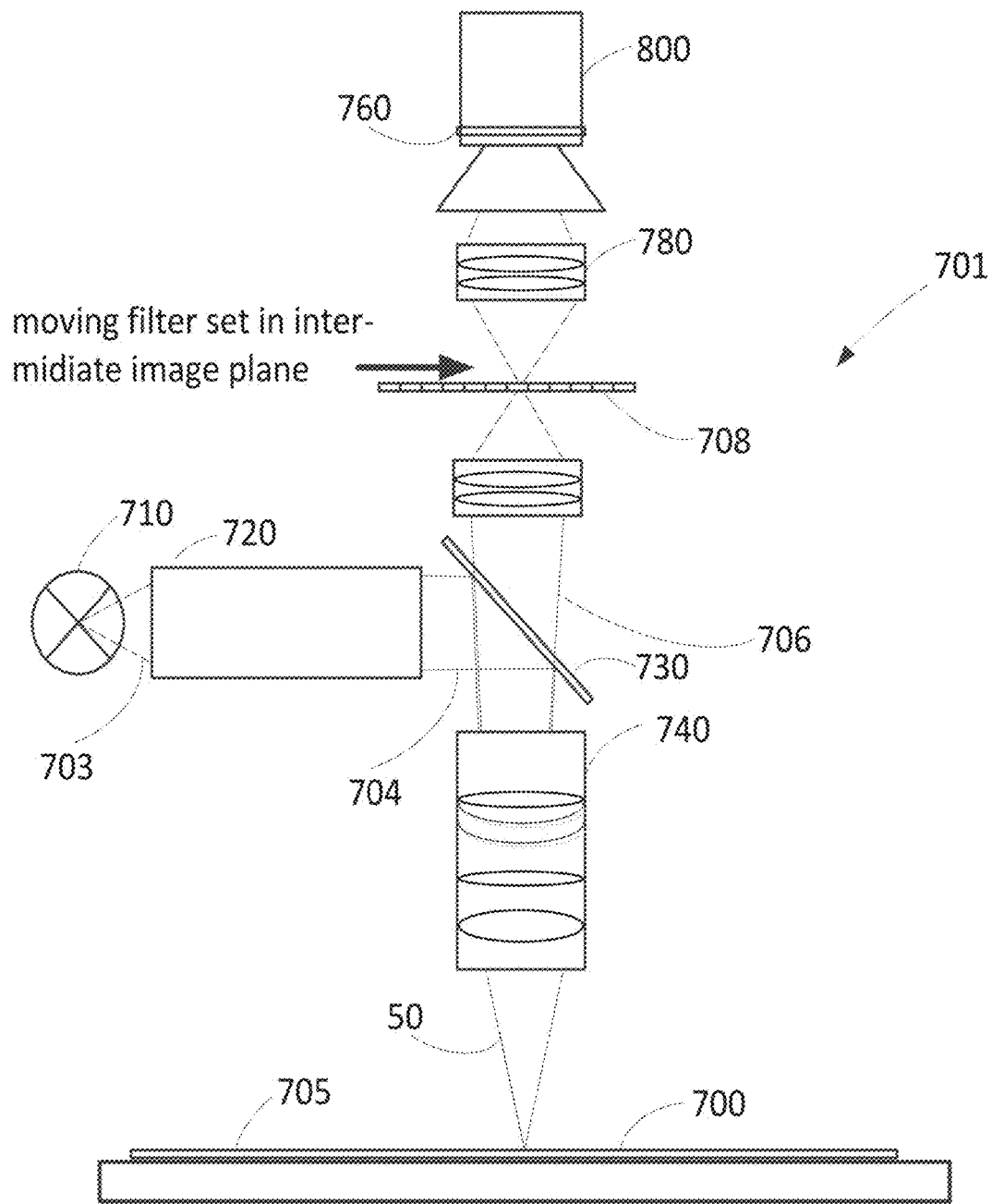
FIG. 1b is a schematic illustration of a device for measuring reflectivity at different wavelengths with a moving filter set in an intermediate plane.

FIGS. 1a and 1b show an assembly 701 to measure the reflectivity of a sample 700 at different wavelength ranges. The sample 700 has a layer stack 702 to be inspected which is shown by example for a two layer situation in greater detail in FIG. 2. Broadband light 703 from a light source 710, such as an LED, a tungsten lamp or an arc discharge lamp, is homogenized by optical means 720. The optical means homogenize the lateral and angular light distribution. This can be achieved by, for example a glass rod with hexagonal or rectangular cross section or a diffusor. The homogenized light is then deflected by a 50% mirror 730 through an objective 740 onto the sample 700. This is represented by the schematically illustrated path of light designated with numeral 704.

The light is partially reflected at the surface 705 of the sample 700. The intensity of the reflected light 706 is modulated. The modulation is caused by the interference effect of light partially reflected at each of the material interfaces as described below with reference to FIG. 2. The light 706 which is reflected back passes the mirror 730. The light is passing tube optics 780 positioned in front of a detector 800 inside a camera. Thereby, an image of the sample 700 is generated on the detector 800. The detector 800 is a high speed array detector with 2560×2160 detector elements. The detector elements are arranged in lines and columns.

The filter means 760 is either incorporated here into the detector assembly of the camera or an intermediate image plane 708 is generated and the filter means is moveably positioned in the intermediate image plane 708. The filter means 760 serves to filter the light at desired locations of the sensor chip of the detector by allowing only certain wavelength ranges to pass. The spectral wavelength selection characteristic of this embodiment is depicted in FIG. 3.

Figure 3:
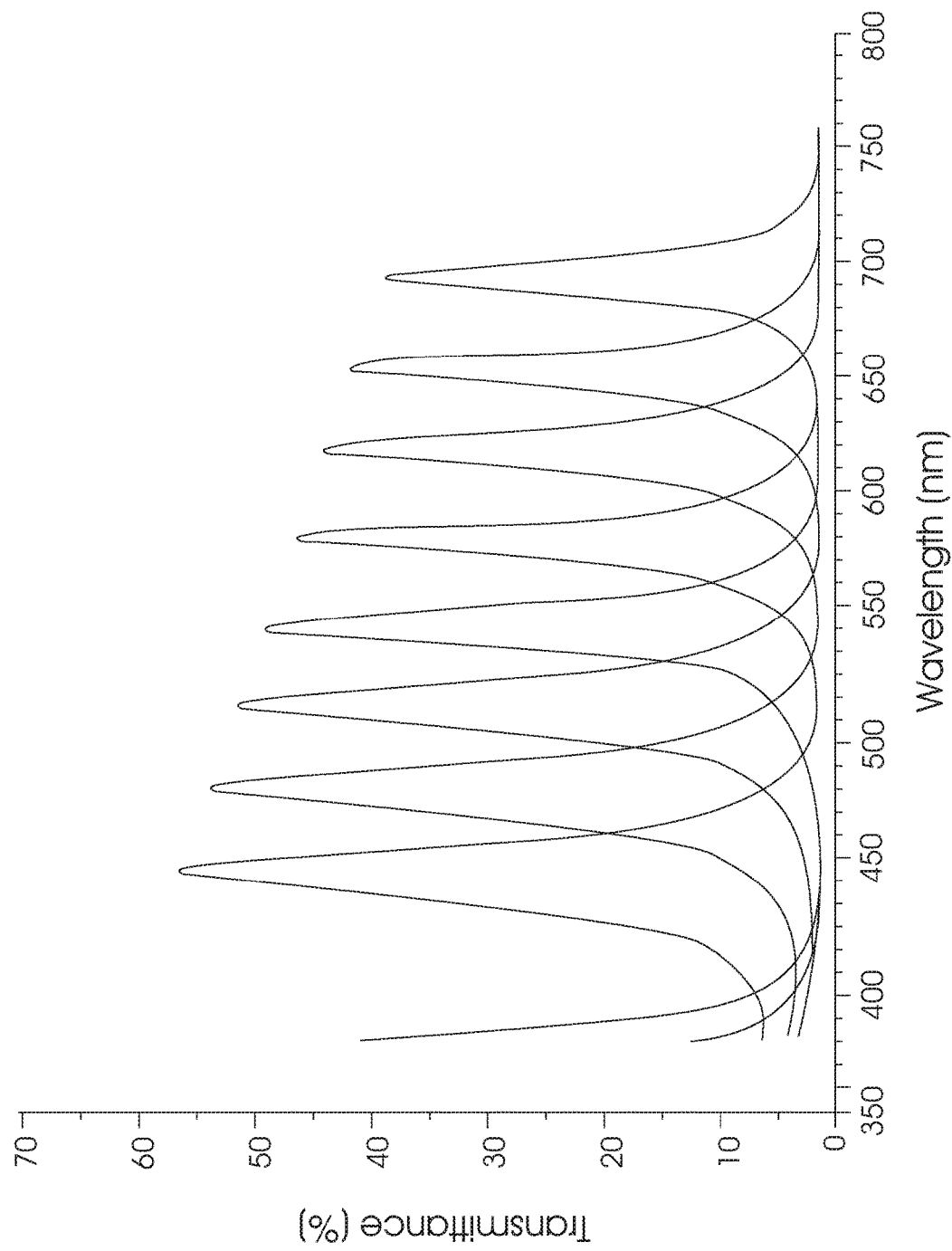
FIG. 3 illustrates an example of the spectral transmission profiles of 6 broadband filters used in the assembly of FIG. 1.
Figure 4B:
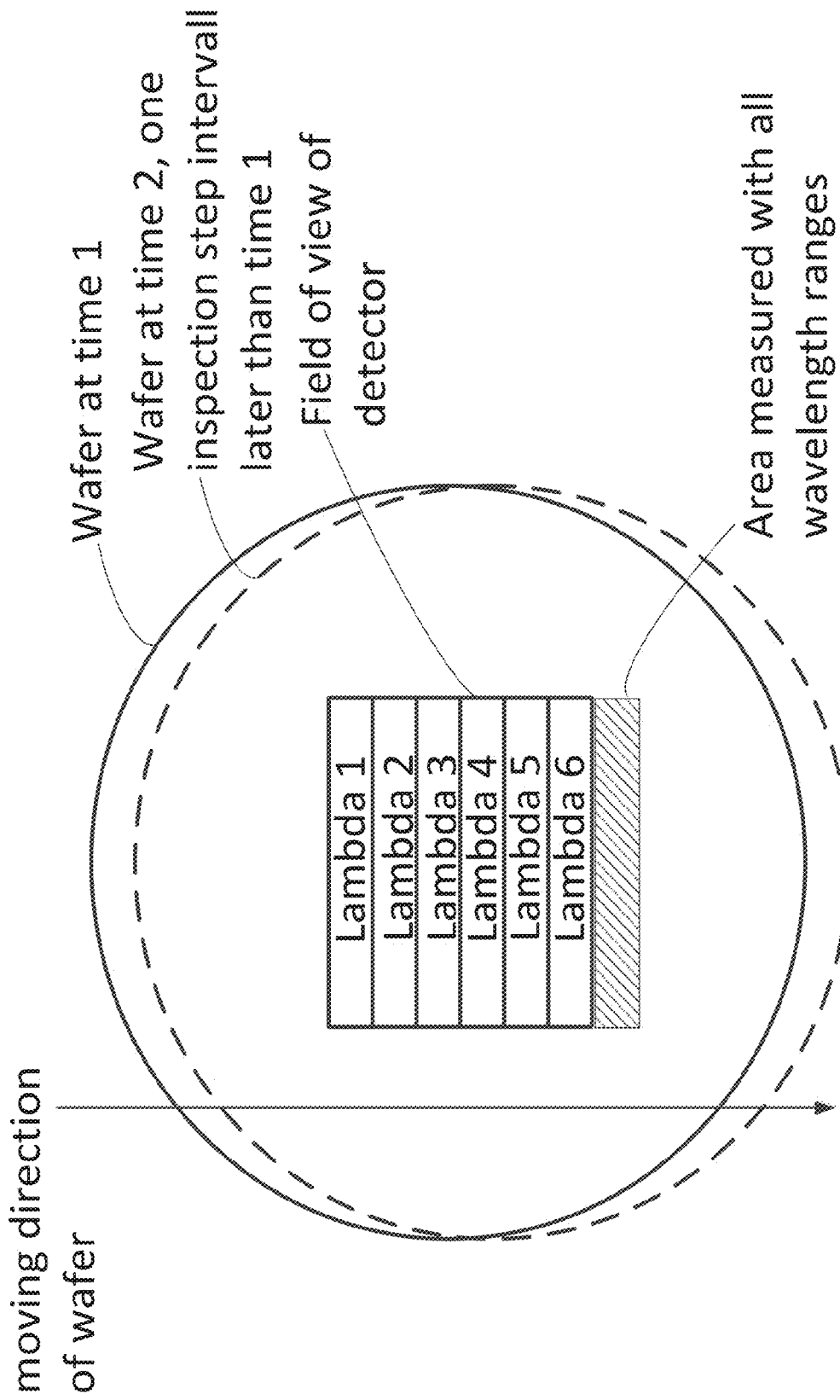
FIG. 4b is a schematic view as in FIG. 4a with the moving stack of layers.

FIGS. 4a and 4b show a front view of the filter means 760. FIG. 4b also schematically shows the inspected wafer at two different measuring times time 1 and time 2. The wafer was moved by moving stage 707 between time 1 and time 2.The filter means 760 consists of 6 parallel stripes 761, 762, 763, 764, 765 and 766 of optical broadband filters in the wavelength ranges designated with the peak values of the transmission profile as illustrated in FIG. 3, lambda 1, lambda 2 . . . lambda 6. Each of the stripes extends along the entire width of the detector array, i.e. 2560 detector elements. The width of the stripes 761, 762, 763, 764, 765 and 766 is one 6th of the width of the detector array in the same direction, i.e. 360 detector elements. The number of 6 filters is, of course, variable and any number of filter stripes may be used.

Thereby, the whole active detector array is divided into 6 sections in the form of parallel stripes extending from one end of the detector to the other. The sections are used for the 6 different wavelength ranges as illustrated in FIG. 3. Each section on the detector comprises 360×2560 detector elements illuminated by each of the 6 wavelength ranges selected by the filter means 760. Hence, at each of these wavelength areas the light intensity for the particular wavelength interval is determined with a resolution of 360×2560 pixels of the sensor assembly 800.

The wavelength characteristic of the described embodiment is shown in FIG. 3. Six wavelength ranges are selected in 6 areas of the filter. The figure shows the wavelength transmission characteristic of each filter. The following table indicates the key parameters of the filter set up.

| FWHM_Mean = 20 nm | Filter_1 | Filter_2 | Filter_3 | Filter_4 | Filter_5 | Filter_6 | Filter_7 | Filter_8 |
|---|---|---|---|---|---|---|---|---|
| Lambda_Pic(nm) | 450 | 484 | 519 | 554 | 590 | 626 | 663 | 700 |
| FWHM(nm) | 26 | 23 | 21 | 20 | 19 | 18 | 17 | 16 |
| T_Max(%) | 57 | 54 | 52 | 49 | 47 | 44 | 41 | 39 |
| T_mean(%)380->800 nm | 5 | 5 | 4 | 4 | 3 | 3 | 3 | 4 |

FWHM is the full width at half maximum. Lambda is wavelength of the maximum intensity. T is the transmission value for the intensity.

Using a multi-element sensor assembly as a detector allows measuring the spatial distribution and homogeneity of the layer thicknesses of the layers very fast. The calculation described below in greater detail can be performed for each detector element of the detector assembly separately. One measurement step, thereby, provides a large number of thickness values of an area or a line of the sample. By adding a movable station 707 to the assembly 701, which provides a relative lateral movement between the detector and the sample 700, it is possible to scan the whole sample surface 705 and create a full map of the thickness values of the whole surface 705.

By using different objectives 740 with different magnification, like it is common practice for microscopes, the lateral resolution of the detector 800 can be adapted to the needs of the measurement task. Hence, it is possible to measure the thicknesses of the layers very accurately and with a lateral resolution as low as a few hundred nanometers with a high speed.

Figure 2:
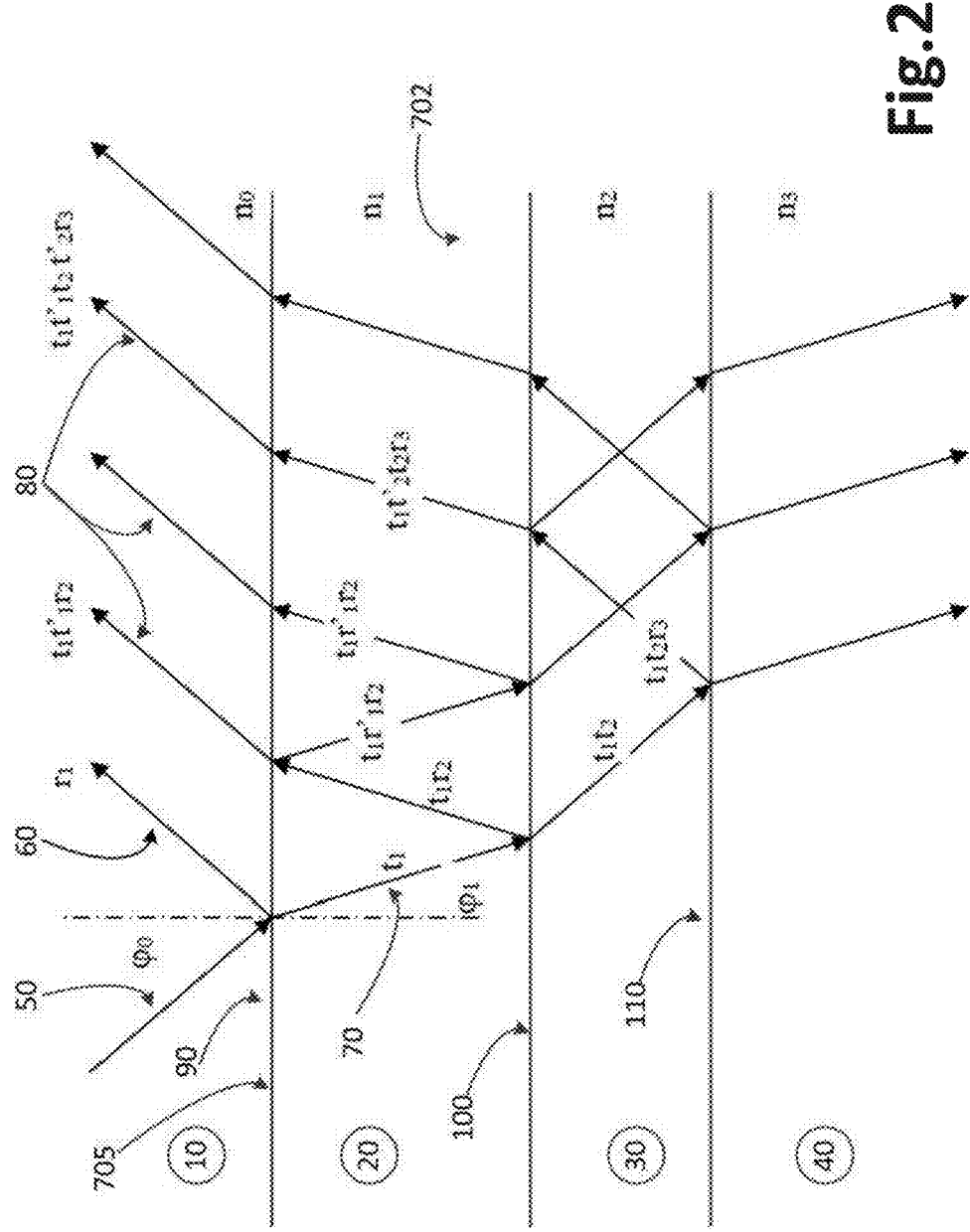
FIG. 2 illustrates the path of the rays in a stack of layers.

FIG. 2 illustrates the physical effects of the reflection at a sample 700. The sample 700 is a so-called double layer stack 702. The double layer stack 702 has a top layer 20 having a refraction index $n_1$ and a buried bottom layer 30 having a refraction index $n_2$. The layers 20 and 30 are stacked on a substrate material 40 having the refraction index $n_3$. While the substrate is part of the stack its thickness is not an issue regarding this invention. Therefore, the substrate does not constitute a "layer" as it is meant here.

The stack 702 is placed in an environment of ambient material 10, which is air in the present embodiment. It may, however, be also vacuum, oil or water. The ambient material 10 has a refraction index $n_0$. As described above, light 50 is incident on the sample surface 705. The light 50 travels through the ambient material 10. The light is partially reflected at the interface 90 between the ambient material 10 and the top layer 20. Thereby, the light 50 is split into the initially reflected light 60 and light 70 transmitted through the interface 90 formed by surface 705 while it is refracted at the same time.

The light is also partially reflected and split into reflected and transmitted light at each further interface 100 and 110 between the materials 20 and 30, and 30 and 40, respectively.

All light incident and reflected on any of the interfaces 90, 100 or 110 between materials 10, 20, 30 or 40 with different refraction indices for multiple times will finally be reflected into ambient space 10. This is represented by the light beams 80. The intensity measured at the detector 800 of light beams 80 will be smaller intensities than the intensity of the incident light 50 due to the repeated reflection and transmission at the interfaces. Since the light 80 is composed of light travelling an additional way through the layer materials 20 and 30, the waves composing the light 80 are delayed in time with different time differences with respect to the initially reflected light 60. This causes interference. Thus, the intensity of the measured intensity including all reflected light 60 and 80 together is modulated by destructive and constructive interferences of light waves 60 and 80 according to their time delays. Since the time delays of light 80 are determined by the thickness of the layers 20 and 30 multiplied by their refraction index $n_1$ and $n_2$, respectively, the modulation of the intensity of the reflected light 80 is a function of the layer thicknesses of layers 20 and 30. Hence, analyzing the intensity modulation can be used to determine the layer thicknesses of the layers 20 and 30 using the refraction indices of the materials which are well known.

The formulas describing this effect are known as Fresnel equations together with the basic principle of the superposition of electromagnetic waves. The functions may also be determined by experiments, such as ellipsometry.

Figure 5:
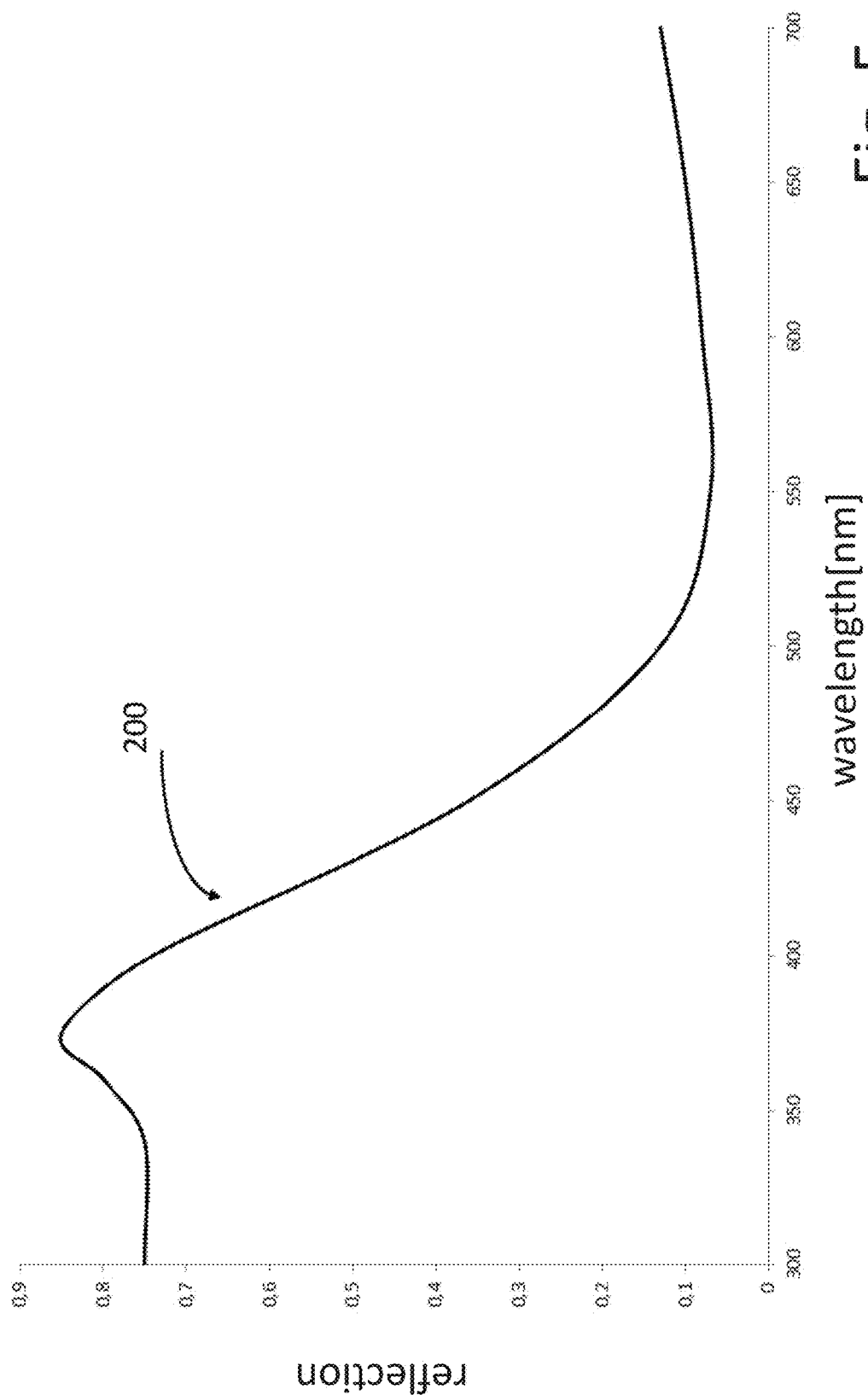
FIG. 5 shows a typical wavelength dependency of the reflection at a multi-layer stack.

If the intensity is determined as a function of the wavelength of the incident light 50 for, for example, a double layer stack with layers 20 and 30 of known material on a substrate 40 of known material within an environment of known ambient material 10, a reflection intensity function will be obtained. A typical reflection intensity function 200 is shown in FIG. 5 for a system with a top layer 20 in the form of a 12 nm silicon layer and a buried layer 30 in the form of a 25 nm silicon oxide layer. The layers 20 and 30 are stacked on top of a substrate 40 of silicon within air as ambient material 10. FIG. 5 illustrates the effect by example and can be repeated for any material/thickness combination. The effective reflection coefficient for the whole ambient/ layers/substrate system 200 is shown on the abszissa versus the wavelength in nm. It can be seen, that light in the range of 400 nm is reflected with a higher intensity than, for example, light in the range above 500 nm.

The measured intensity of the reflected light changes if the layer thickness of layer 20 or 30 changes. The change can be expressed mathematically in the form of the partial derivatives of the reflection divided by the layer thickness.

Figure 6:
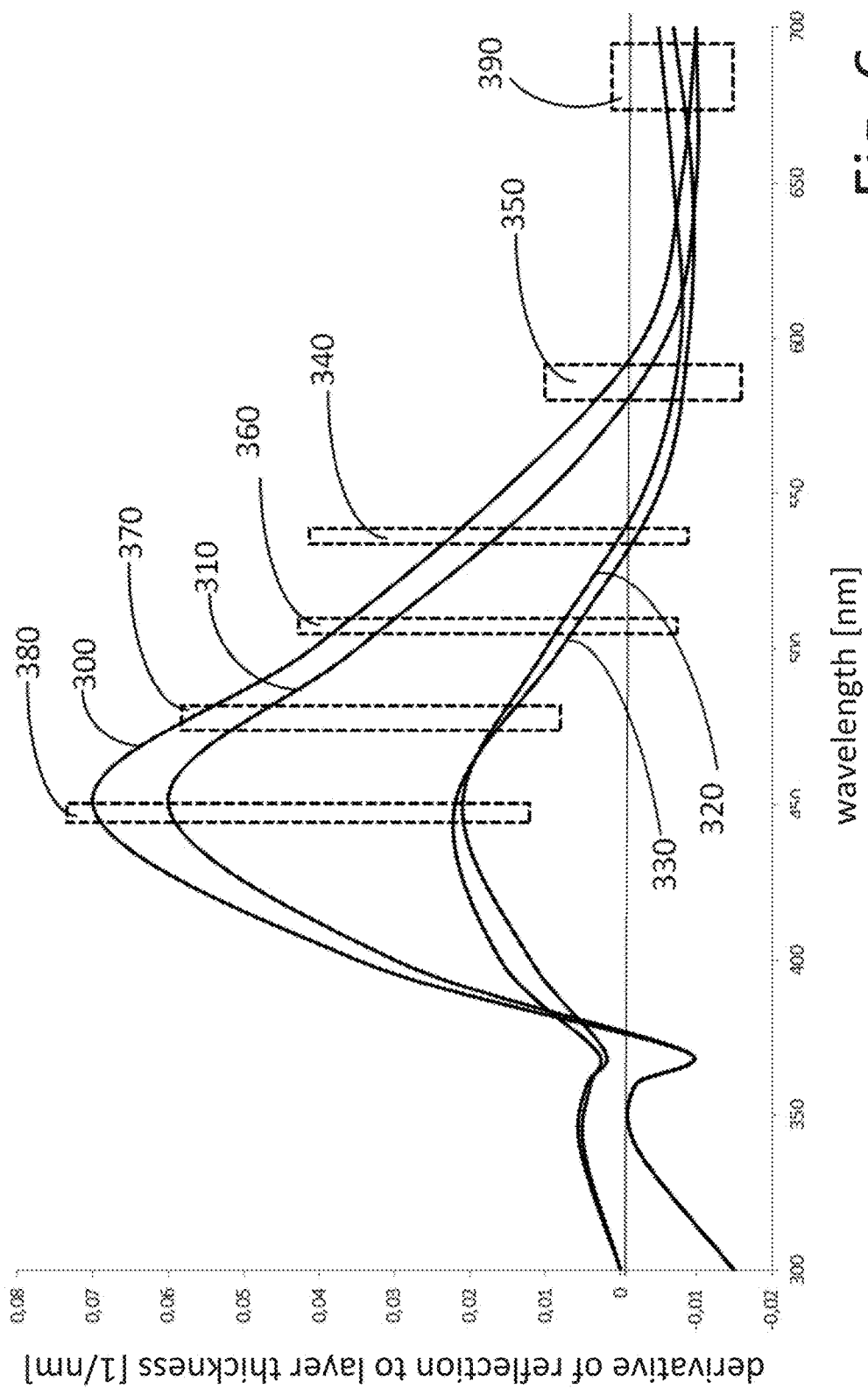
FIG. 6 shows a typical wavelength dependency of the change of reflection at a multi layer stack.

FIG. 6 shows such ratio for the same wavelength range between 300 nm and 700 nm as FIG. 2. The curves 300 and 310 illustrate the influence of a change of the thickness of the silicon top layer 20. Curve 310 illustrates such influence with a slightly different thickness of the oxide layer 30. In the same manner 320 and 330 show the influence of a change in the thickness of the buried oxide layer 30. Curve 330 represents a slightly different thickness of the silicon layer 20 compared to the nominal silicon thickness used for 320.

The dashed box 340 schematically illustrates a first wavelength range to measure the thickness of the silicon layer 20. Known methods assume, that due to the nearly zero value of the derivative of the reflection to oxide thickness as shown by 320 and 330 the influence from the thickness of the oxide layer 30 is much smaller than the influence of the thickness of the silicon layer and may be therefore ignored. However, since obviously curves 300 and 310 are not identical in the wavelength range 340 such neglection produces a systematic error.

The present embodiment, therefore, uses further wavelength intervals 350, 360, 370, 380, 390 for further measurements, which are quasi independent from each other. The wavelength ranges are defined by the filters shown in FIG. 4 with transmission profiles shown in FIG. 3. The thickness layer values will be obtained by using the data from the independent measurements of the reflection at different wavelength intervals 340, 350, 360, 370, 380, and 390. Since only two layers are inspected with 6 wavelengths in the present example, there is a certain amount of oversampling. This oversampling serves to improve accuracy of the results. Up to 6 layers may be inspected with 6 different wavelengths if calibration curves are used. Obviously, any other amount of layers may also be inspected if a suitable amount of wavelength ranges is selected.

It is understood, that such calculations can be performed for any number of layers in the stack. The matrix formalism for the calculation of the layer to layer effect based on Fresnel equations is well known in the art.

In order to obtain thickness values from reflectivity measurements a calibration is carried out. The prior art methods correlate the measured gray value to the "real" thickness values of the layers. Such "real" values are obtained by, for example, ellipsometry. It is also possible to use straight forward calculations of the reflected light from the known material parameters for several thicknesses. In a real embodiment ellipsometry will, however, provide a good reference method.

Figure 7:
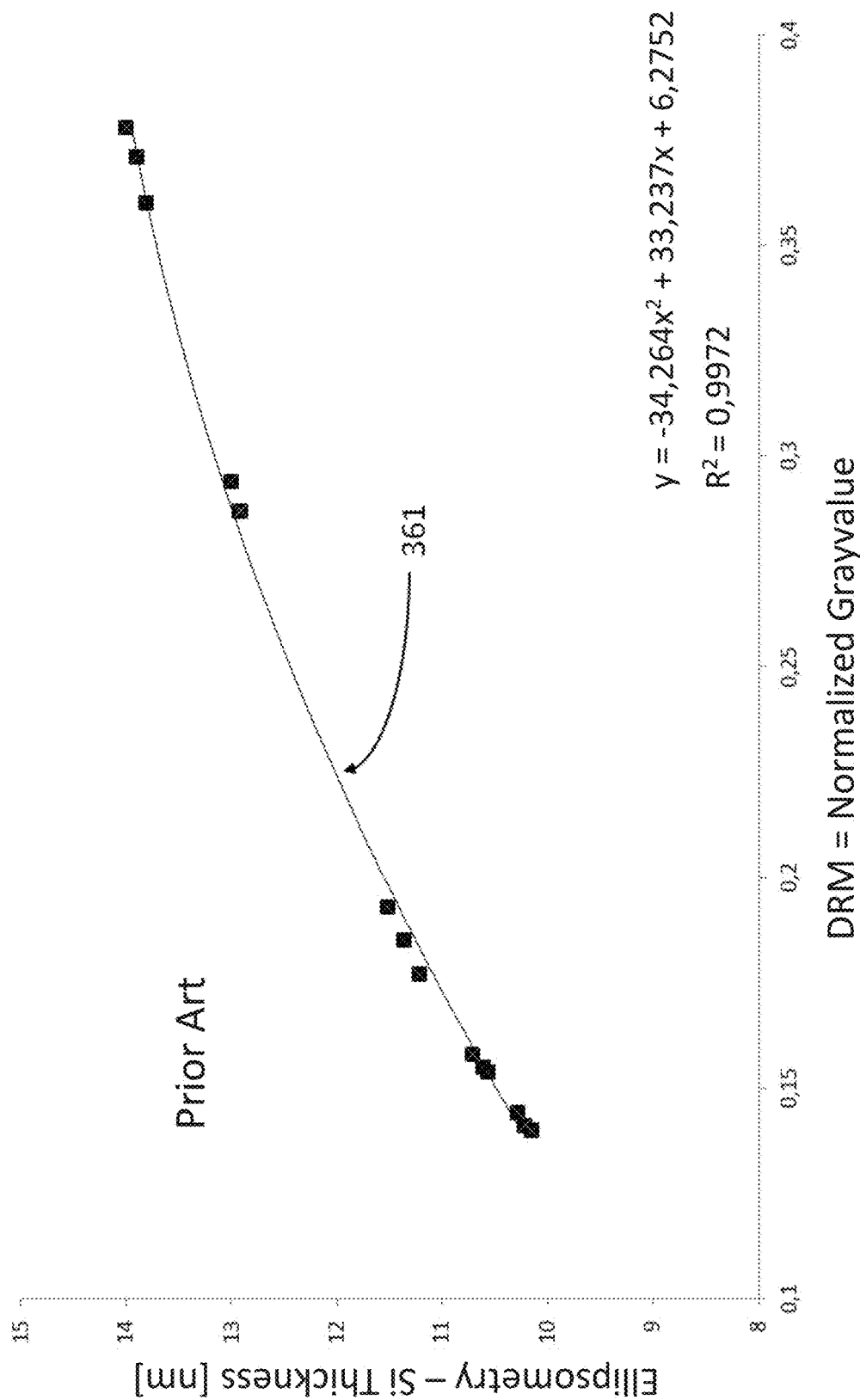
FIG. 7 shows a typical calibration curve obtained with ellipsometry.

FIG. 7 shows a calibration curve 361 according to the prior art for a double layer system with a 25 nm thick buried bottom oxide layer and various samples having different silicon layer thicknesses. The reflectivity measurement is made under quasi monochromatic light conditions using only one small wavelength interval in the wavelength range 340 as illustrated in FIG. 6. The reflected intensity is taken for this purpose as measured intensity normalized against some reflection standard, in order to exclude apparatus influences. The advantage of the approach using measured values and comparing them with a reference method result is to avoid misinterpretations due to other effects, like e.g. optical effects, of the embodiment. The accuracy of the resulting calibration curve can be further enhanced by deriving the form of the curve from the theory by calculating the reflection intensity straight forward from known material parameters and thickness values measured by the reference method and searching for a best fit to the measured gray values.

Figure 8:
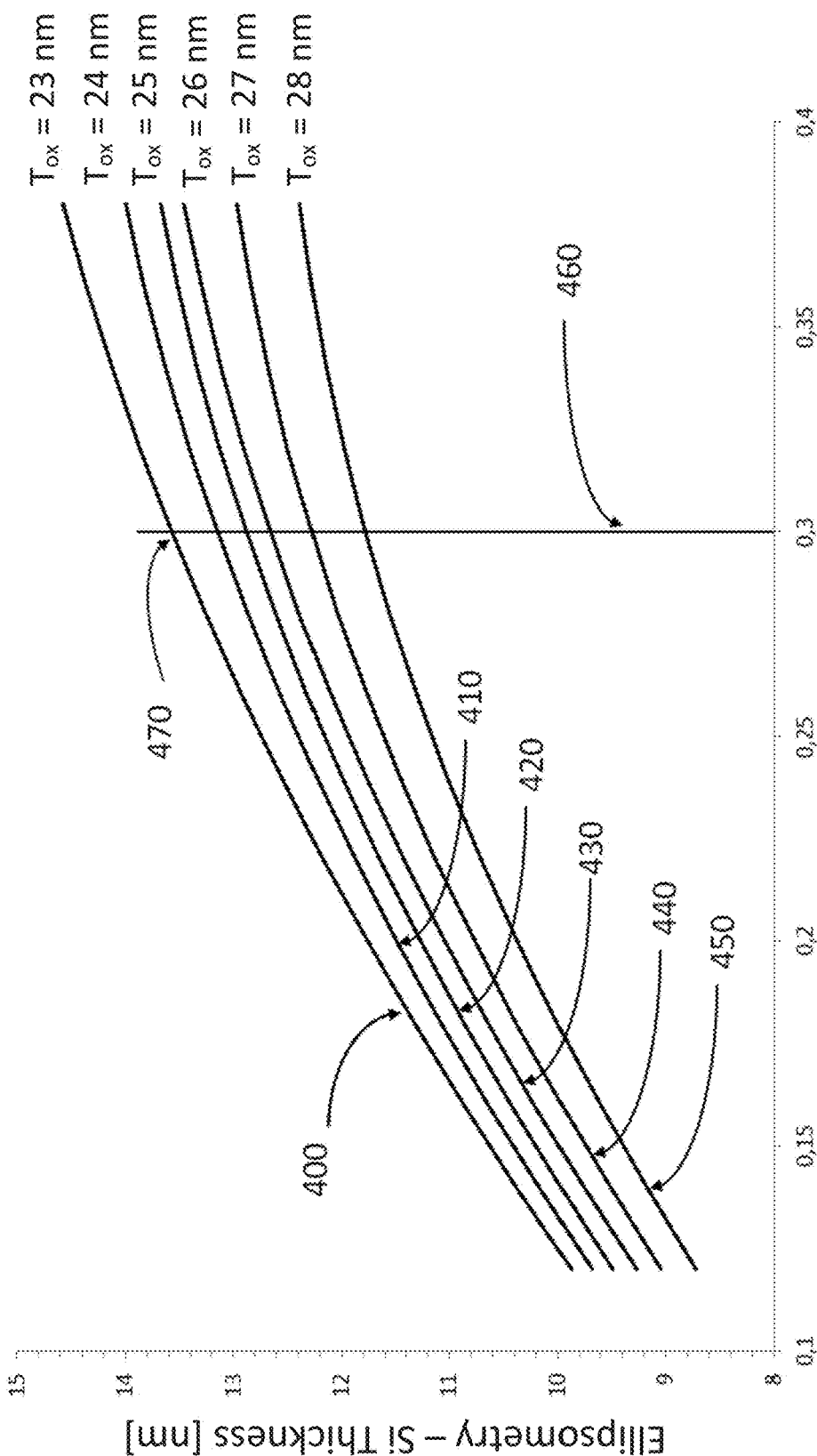
FIG. 8 shows a series of calibration curves for several samples of stacks.

The embodiment of the present invention calibrates by repeating the same procedure as used for the calibration curve 360 in FIG. 7 for a series of samples with different thicknesses of oxide layer 30. Thereby, a series of calibration curves 400, 410, 420, 430, 440, and 450 are obtained which are shown in FIG. 8. Calibration curve 400, for example represents the relation between different thicknesses of the silicon layer 30 and the measured intensity for a sample having a thickness of the oxide layer 30 of 23 nm. Calibration curve 410 shows the same with an oxide layer 30 having a thickness value of 24 nm. Samples with different thicknesses of the oxide layer 30 and with different thicknesses of the silicon layer 20 are measured. Again, all reflectivity measurements are carried out at first with light from one small wavelength interval within the range 340.

If ellipsometry is used as reference method for the determination of the silicon thickness, the oxide layer thickness is checked at the same time and the data value pairs sorted accordingly.

With such calibration curves, as shown in FIG. 8 unknown samples of the same material system but with unknown layer thicknesses can be inspected by measuring a specific reflectivity value. For example, if the normalized reflectivity gray level value is 0.3 as illustrated by the straight line 460 in FIG. 8, the crossing points of the measured reflectivity in the calibration curves 400, 410, 420, 430, 440, and 450 provide the relation between possible thickness values of the silicon layer 20 and the oxide layer 30. The point 470, for example, denotes a first possible combination of a thickness of the oxide layer 30 of 23 nm and a thickness of the silicon layer 20 of 13.6 nm (value on ordinate axis) fulfilling the measured reflectivity level at the line 460. This relation can be established for each calibration curve.

In other words: the measurement of the reflected intensity of an unknown sample at one wavelength will provide a plurality of possible thickness combinations which may be represented by a function. Such a function is represented in the form of curve 500 in FIG. 7. In order to select the correct values, the measurements are repeated in a second wavelength interval. In the present embodiment the interval in the wavelength range 350 (see FIG. 4) is used. The result is represented by curve 510 in FIG. 9.

Figure 9:
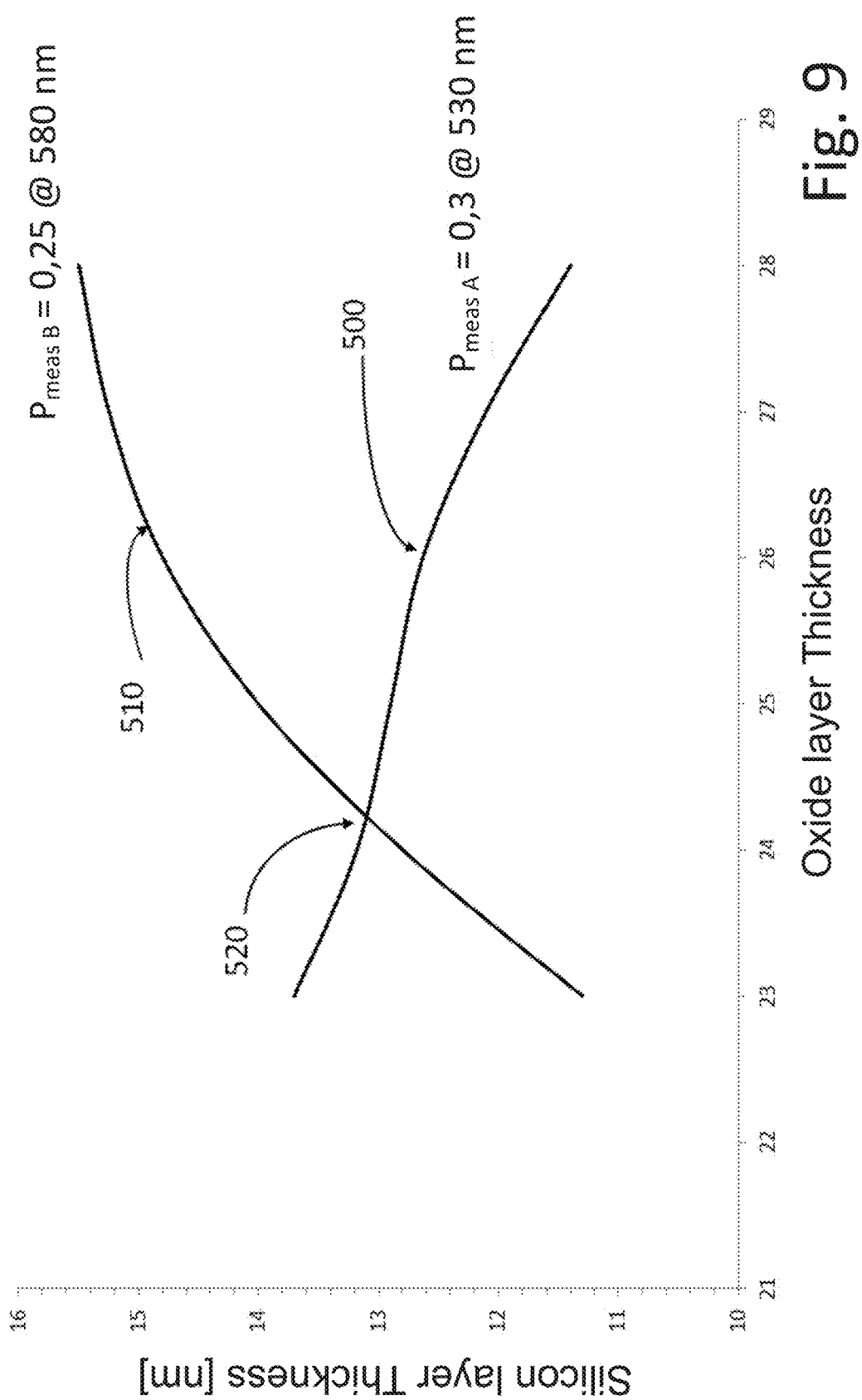
FIG. 9 illustrates the correlation between possible thickness values of two different layers at different wavelengths.

A plurality of curves like curves 500 and 510 exist for any of those pluralities of measurements using different small wavelength intervals of incident light. Any such pair of curves has just one crossing point 520 where the measured reflection levels are obtained at the same time from the same two layer thickness values. In the example of FIG. 9 this results in a silicon layer thickness of 13.14 nm and an oxide layer thickness of 24.2 nm.

Generalizing this approach to m wavelength ranges establishing m measurements and n unknown parameters where parameters may be layer thicknesses or material compositions one gets the following consideration. For the m different wavelength ranges, i.e. quasi-independent measurements, the dependencies of the m reflected intensities in the m wavelength ranges can be expressed by m surfaces in n+1-dimensional spaces. The n dimensions are the n parameters, i.e. layer thicknesses or material compositions. The $n+1^{st}$ dimension is the intensity in the considered wavelength range. Each of the m wavelength ranges establishes such an n+1 dimensional space where the surface describes the functional dependency of the reflected intensity from the n parameters.

Each of the m measured intensities in the m wavelength ranges now define an n-dimensional curve on the respective surface describing the possible solution vectors for this particular intensity value measured. These m curves having n dimensions have at least one crossing point in common. This crossing point is the final solution vector, characterized by having the same n parameters and being a point of all m surfaces. Mathematically this final solution vector is found by solving the equation set of m equations with m vectors with n vector elements. Of course m, i.e. the number of quasi-independent measurements, has to be higher or equal than n, the number of unknown parameters like layer thicknesses or material compositions.

2. Embodiment: Measurement of One $SiO_2$-layer on Silicon

Figure 10:
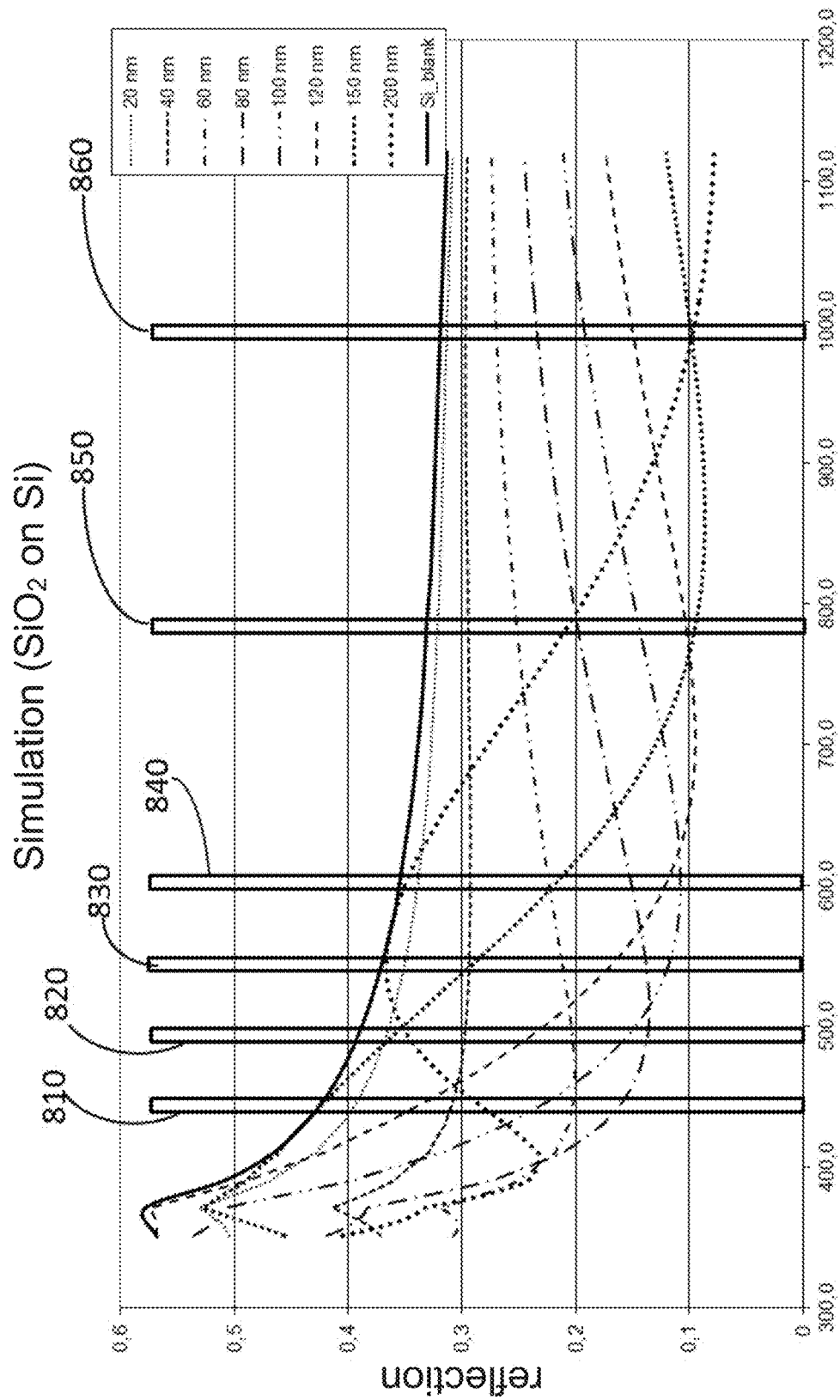
FIG. 10 illustrates a typical wavelength dependency of the change of reflection at a two layer stack for different thicknesses of a SiO2-layer on silicon and different wavelength ranges which are used for measurements.

FIG. 10 illustrates a different embodiment where the same measurement set-up was used as described above for the first embodiment. The present embodiment, however, measures only one layer thickness value which is the thickness of a $SiO_2$-layer on silicon. The reflection function may be simulated and the simulation can be adapted to the values by fitting with, for example, a Levenberg-Marquardt-algorithm. The thicknesses of the layer range from 20 nm to 200 nm. Six wavelength ranges are used for the measurements which are designated with numerals 810, 820, 830, 840, 850 and 860. Since six values are measured for only one unknown thickness value the statistic error will be increased. Also, the measuring range is increased: The wavelength range 820 at about 500 nm, would not allow distinguishing between the thickness values 20 nm, 150 nm and 200 nm. With such a measurement alone the result would be ambiguous. The measurement at several different wavelength ranges will allow distinguishing such cases.

In theory there are some restrictions for the measurable parameters. Parameters may be here any layer characteristic which influences the optical properties of the layer stack as a whole (more exact which influences the refraction index and/or extinction coefficient). The most prominent examples of such parameters are the individual layer thicknesses and the material compositions. The set of equations is either unambiguously solvable and there is exactly one set of parameters. Alternatively, if at least two of the parameters have an exactly identical effect on the reflection in all n wavelength ranges or the effects compensate each other, a plurality of solutions may exist. Also, the method is limited to the range where the Fresnel-equations will not provide another solution due to its periodic nature. The periodicity of the Fresnel-equations will limit the method especially to thick layers.

It is clear, that the given embodiment is only an example to illustrate the method according to the present invention. Similarly, the method can be used for any other material and/or thickness combination of a two layer stack on a substrate. Examples are, among others, strained silicon, silicon-germanium, germanium, gallium-arsenide, indium-phosphide, indium-arsenide, indium-gallium-arsenide, mercury-telluride, III-V and II-VI ternary and quaternary semiconductor alloys, other oxides and nitrides, photo resists, thin metal layers, glass, quartz and plastic materials.

From the above discussion it is also obvious, that the used wavelength intervals must not be selected such that the dependency of the reflection from one of the layer thickness values is minimized. They can be selected more freely e.g. to provide a high and approximately similar signal level for the reflection measurement to improve the measurement stability. The wavelength intervals are used to maximize the resolution of the measurement.

The present invention does not only enable the determination of the thickness of a layer but also the determination of the material composition.

What is claimed is:

1. A method for determining the thickness of one or more layers of a sample stack of layers or other properties influencing the intensity of light reflected by said sample stack of layers with an assembly comprising:
    a light source emitting light for illuminating said sample stack of layers, said sample stack of layers reflecting said light from said light source with an intensity; and
    a camera with an array detector with a plurality of detector elements arranged in lines and columns for detecting said intensity of said light reflected by said sample stack of layers; and
    means for separating said intensity of said light reflected by said sample stack of layers in defined wavelength ranges, said defined wavelength ranges being at least partly different from each other;
    the method comprising the steps of:
    illuminating said sample stack of layers with said light from said light source;
    detecting said intensity of light reflected by said sample stack of layers with said detector in different wavelength ranges; and
    determining the thickness or other property from said intensity detected by said detector;
    and wherein
    an image of said sample stack of layers is generated on said detector;
    said detector comprises a plurality of sections in the form of parallel stripes, said stripes detecting said intensity of said light reflected by said sample stack of layers simultaneously;
    light of one of said wavelength ranges only is detected by each of said plurality of sections of said detector; and
    said parallel stripes have a longitudinal direction and a movement of said image of said sample stack of layers on said detector or of said parallel stripes is generated in a direction perpendicular to said longitudinal direction of said parallel stripes such that each point of said inspected sample stack of layers is detected at least once in each of said different wavelength ranges.

2. The method of claim 1, and wherein said detector elements in the same section of said detector are sensitive to one of said different wavelength ranges only.

3. The method of claim 1, and wherein said light travels along an optical path and said light in said optical path between said light source and said detector is filtered by a plurality of different bandpass filters in a striped geometrical order, each bandpass filter transmitting light in one of said wavelength ranges only and positioned in an object plane, a detector plane, an intermediate image plane or any other plane conjugated to said sample stack of layers.

4. The method of claim 1, and wherein a series of images is taken with said detector and a movement of said image of said sample stack of layers on said detector or a movement of said parallel stripes is generated before each of said images of said series of images is taken, the length of said movement corresponding to the width of said sections on said detector.

5. The method of claim 1, and wherein the amount of different wavelength ranges is identical to the amount of said stripes.

6. The method of claim 1, and wherein said sample stack of layers has less layers than wavelength ranges and the thickness and/or other property of at least one layer is determined from two or more measurements.

7. The method of claim 6, and wherein the thickness and/or other property of at least one layer is determined from a plurality of measurements without a measured calibration curve.

8. The method of claim 7, and wherein the thickness and/or other property determined without a measured calibration curve is calculated using theoretical values of material properties of said layers.

9. The method of claim 1, and wherein a measured calibration curve is used for each inspected layer to determine the thickness and/or other property.

10. An inspection assembly for determining the thickness of one or more layers of a sample stack of layers or other properties influencing the intensity of light reflected by the sample stack comprising:
    a light source emitting light for illuminating said sample stack of layers, said sample stack of layers reflecting said light from said light source with an intensity; and
    a camera with an array detector with a plurality of detector elements in lines and columns for detecting said intensity of light reflected by said sample stack of layers in defined, different wavelength ranges; and
    computing means for determining the thickness or other property from said intensity detected by said detector;
    and wherein
    optical means are provided for generating an image of said sample stack of layers on said detector;
    said detector comprises a plurality of sections in the form of parallel stripes, said stripes adapted to simultaneously detect said light reflected by said sample stack of layers;
    filter means are provided for transmitting only light of one selected wavelength range to only one of each of said plurality of sections of said detector or detector elements adapted to measure light of one selected wavelength range only in each of said plurality of sections; and
    said parallel stripes have a longitudinal direction and moving means are provided for moving said image of said sample stack of layers on said detector or of said parallel stripes in a direction perpendicular to said longitudinal direction of said parallel stripes such that each point of said inspected sample stack of layers is detectable at least once in each of said different wavelength ranges.

11. The inspection assembly of claim 10, and wherein said detector elements in the same one of said sections of said detector are sensitive to one of said different wavelength ranges only.

12. The inspection assembly of claim 10, and wherein a plurality of different bandpass filters in a striped geometrical order is provided in an object plane, a detector plane, an intermediate image plane or any other plane conjugated to said sample stack of layers between said light source and said detector, each bandpass filter transmitting light in one of said different wavelength ranges only.

13. The inspection assembly of claim 10, and wherein the amount of different wavelength ranges is identical to the amount of stripes.

14. The inspection assembly of claim 10, and wherein said detector is formed by a multi-color line camera with a plurality of wavelength ranges.

15. The inspection assembly of claim 14, and wherein the lines of said line camera detector are formed by TDI (time delayed integration) sensor blocks.

* * * * *